(12) United States Patent
Holt et al.

(10) Patent No.: US 6,740,341 B1
(45) Date of Patent: May 25, 2004

(54) TASTE MASKING RAPID RELEASE COATING SYSTEM

(75) Inventors: Kris E. Holt, Maple Grove, MN (US); Rajendra K. Khankari, Maple Grove, MN (US); John Hontz, Plymouth, MN (US)

(73) Assignee: Cima Labs Inc., Eden Prairie, MN (US)

( * ) Notice: Subject to any disclaimer, the term of this patent is extended or adjusted under 35 U.S.C. 154(b) by 0 days.

(21) Appl. No.: 09/449,851

(22) Filed: Nov. 24, 1999

Related U.S. Application Data

(60) Provisional application No. 60/110,032, filed on Nov. 25, 1998.

(51) Int. Cl.[7] ............................ A61K 9/14; A61K 9/16
(52) U.S. Cl. .................. 424/490; 424/494; 424/497; 514/974
(58) Field of Search ................. 424/489–502; 514/974

(56) References Cited

U.S. PATENT DOCUMENTS

| | | | |
|---|---|---|---|
| 4,831,058 A | 5/1989 | Pankhania et al. | 514/570 |
| 5,004,595 A | 4/1991 | Cherukuri et al. | 424/48 |
| 5,085,868 A | 2/1992 | Mattsson et al. | 424/490 |
| 5,234,957 A | 8/1993 | Mantelle | |
| 5,516,524 A * | 5/1996 | Kais et al. | |
| 5,527,545 A | 6/1996 | Santus et al. | 424/490 |
| 5,614,222 A * | 3/1997 | Kaplan | |

* cited by examiner

*Primary Examiner*—Gollamudi S. Kishore
(74) *Attorney, Agent, or Firm*—Lerner, David, Littenberg, Krumholz & Mentlik, LLP

(57) ABSTRACT

The present invention relates to a core containing a drug encased in a spacing layer and a taste masking layer which provides effective taste masking for in-mouth disintegrable dosage forms containing highly objectionable tasting drugs, as well as dosage forms containing these cores.

17 Claims, 1 Drawing Sheet

TASTE MASKING RAPID RELEASE COATING SYSTEM

The present invention claims the benefit of the U.S. Provisional Application No. 60/110,032 filed on Nov. 25, 1998, the disclosure of which is incorporated by reference herein.

FIELD OF THE INVENTION

The present invention relates to the fields of medicine and pharmacy and particularly to providing effective taste masked dosage forms which facilitate compliance by patients.

BACKGROUND OF THE INVENTION

Patients who will not or cannot swallow, such as young children, the very elderly and patients with dysphagia constitute a significant challenge to the pharmaceutical industry. The industry has met that challenge by developing a number of drug delivery protocols, including rapid in-mouth disintegrating tablets, tablets which disintegrate in liquid prior to ingestion, liquids and syrups, gums and even transdermal patches. Unfortunately, each of these methods can pose their own problems.

Transdermal patches can be inconvenient or uncomfortable. They can also be quite expensive to produce. The flux of drug through the skin can also raise very complex dosing issues. Liquids are particularly useful for children. However, liquids can be inconvenient for adults and can be relatively expensive to formulate, package and transport. Tablets which can be dissolved in a liquid before ingestion can also be useful. However, they can also be quite inconvenient in that they require that a liquid and drinking container be provided. Time is required for disintegration or dissolution even when effervescent tablets are used. Finally, these materials can be quite a mess as they can leave a particulate and/or scum in the glass. In-mouth disintegrable dosage forms such as chewables and self disintegrating tablets offer great convenience. Self disintegrating tablets and/or chewables, however, present real taste masking problems as the act of chewing can disrupt protective coatings. They are of ten very soft, making it difficult and expensive to formulate, package and store. In addition, particularly as compared to tablets which are swallowed, taste masking can become a significant obstacle due to the length of exposure in the patient's mouth.

Of course, there are a variety of ways of taste masking various drugs. These include the use of flavorings, sweeteners, effervescent systems and various coating strategies. But for certain drugs and in particular antibiotics, such as gatifloxacin, traditional taste masking has not proven sufficiently effective. In addition, some of these taste masking strategies cannot adapt well to the demands of rapidly dissolvable dosage forms and/or can be quite expensive.

Modified celluloses such as hydroxypropylmnethylcellulose (HPMC), ethylcelluloses and mixtures of such celluloses have been used to produce enteric coatings as well as coatings which can provide a controlled drug release. Controlled release means either an extended release or a rapid release in the small intestine. Such coatings have also be used in taste masking. For many drugs they are acceptable not only for taste masking but also for providing a desired release. However, such coatings were found to be ineffective when it came toe orally disintegrating tablets containing gatifloxacin. Without wishing to be bound by a particular theory of operation, it is believed that, when exposed to saliva in the mouth during the disintegration of the tablet, at least a portion of the coating dissolves or swells, thereby exposing the offending drug to the patient's taste buds. Another product, Eudragit E100 which is a mixture of methylaminoethyl methacrylate and neutral methacrylic acid ester has also been known for use in taste masking, particularly in combination with celluloses such as a cellulose esters. However, these mixtures, as well as Eudragit E100 alone, were found to be ineffective in providing taste asking when using certain objectionable tasting drugs. Therefore there still remains a need for effective taste masking strategies, particularly for use with aggressively bad tasting drugs, which lend themselves to in-mouth rapidly dissolving dosage forms.

SUMMARY OF THE INVENTION

The present invention relates to the discovery of a coating system useful for completely taste masking objectionable tasting drugs. In a preferred embodiment, the taste masking is accomplished without significantly altering the release and availability of the drug.

In accordance with the present invention, there is provided a taste masked formulation which includes a taste masked formulation which rapidly releases in the stomach of a patient comprising:

A drug containing core;

A taste masking layer composed of a material which is generally insoluble in saliva at a neutral to basic pH and completely soluble in saliva at a pH of less than about 6.5; and A spacing layer surrounding said core and substantially completely sequestering said core from said taste masking layer; said taste masking layer preventing exposure of said spacing layer in the mouth of a patient for a period of at least about 20 seconds after being placed into the mouth.

The taste masking layer must be capable of rapidly exposing the spacing layer when the formulation reaches the patient's stomach. In a particularly preferred embodiment, the taste masked formulation is a rapid release formulation capable of rapidly exposing the contents of the core when introduced to the patient's stomach.

Merely applying thicker layers of coating materials can be an ineffective method of taste masking certain objectionable drugs. Thick coatings can cause problems both in terms of size and cost. They can also raise problems in that they may interfere with the desired release profile of the drug. It has been found, however, that by coordinating the right types of coating materials, it is possible to completely mask the taste of particularly objectionable drugs while, at the same time, not adversely affecting the intended drug release profile. This is particularly critical in the context of rapid release dosage forms. By "rapid release," it is understood that the taste masking system should provide little or no interference with the solubility and bioavailability of the drug when compared to the same drug administered in, for example, elixir or solution form.

The use of a spacing layer in combination with a taste masking layer has been found to be particularly effective. Without wishing to be bound by any particular theory, it is believed that drugs, even granulated formulations, can interfere with taste masking coatings. Fines, abrasions, variable coating thickness and the like can all lead to situations where the taste mask coating is compromised. With certain aggressively bad tasting drugs, even a little exposure is too much. This is particularly problematic where the taste mask coating used is one which is designed to dissolve rapidly at acidic pHs. When such coatings are held in the mouth of a patient during the tablet's disintegration, a neutral to slightly acidic pH can sufficiently undermine taste masking so as to expose the patient to objectionable tasting drugs. Using a spacing layer to substantially sequester the drug from the taste masking layer helps reduce or eliminate such coating imperfections. It also acts to delay contact between the drug and the taste buds of a patient upon partial or total failure of the taste masking layer in the patient's mouth. There is also provided a dosage form which includes a dosage form intended for direct oral administration, comprising: an effective amount of at least one drug, said drug present in the cores of coated particles, said cores including a taste masking layer composed of a material which is generally insoluble in saliva at a neutral to basic pH and completely soluble in saliva at a pH of less than about 6.5 and a spacing layer surrounding said core and substantially completely sequestering said core from said taste masking layer; said taste masking layer preventing exposure of said spacing layer in the mouth of a patient for a period of at least about 20 seconds after being placed into the mouth; and at least one pharmaceutically acceptable excipient provided in an amount of between greater than zero and about 100%, based on the weight of the finished dosage form.

DETAILED DESCRIPTION OF THE PREFERRED EMBODIMENTS

Figure 1:
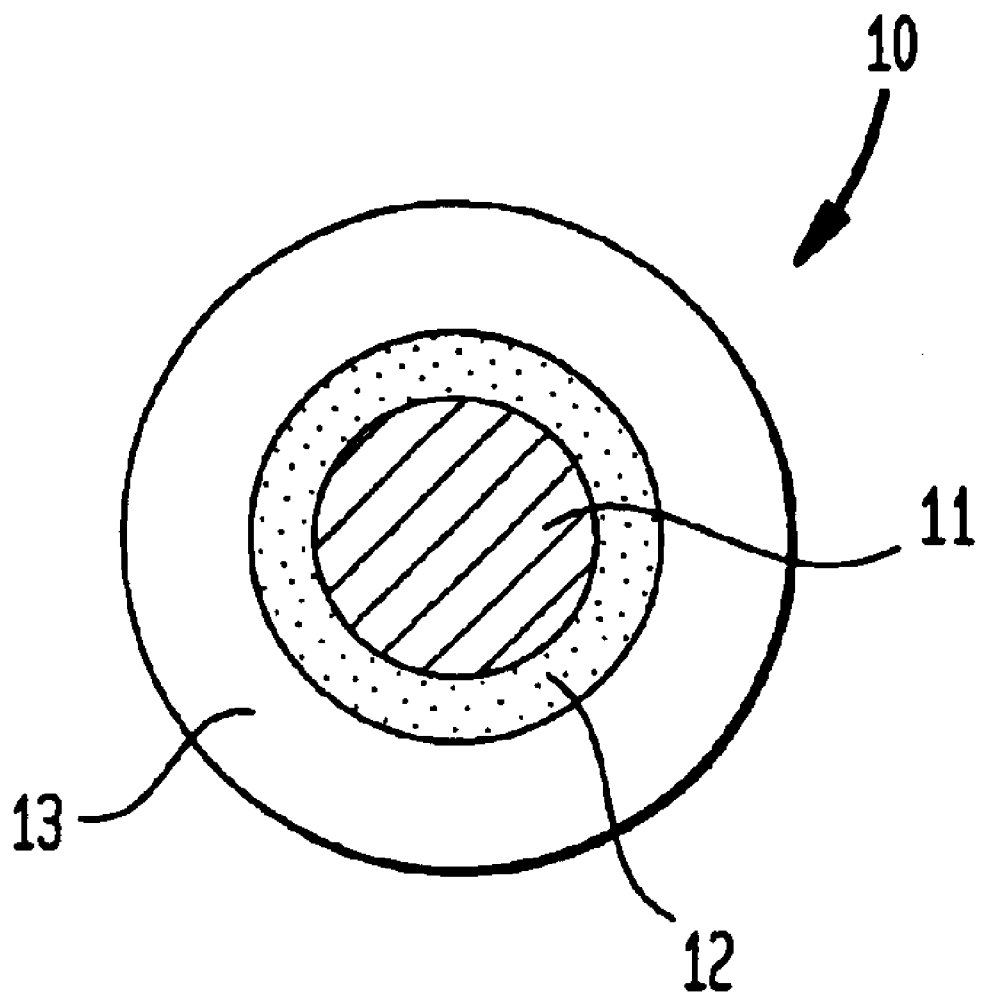
FIG. 1 is an illustration of a coated particle in accordance with the present invention.

The present invention can be used for any material whether objectionable tasting or not. However, where the underlying material is not objectionable tasting, there may be no need to resort to the added steps of applying the compound coatings of the present invention. For particularly obnoxious drugs such as, for example, gatifloxacin, dextromethorphan, acetaminophen, ibuprofen, ketoprofen, aspirin and pseudoephedrine, however, where any risk of exposure of the drug within the patient's mouth is unacceptable, the present invention is indispensable.

The present invention can best be explained by reference to FIG. 1. A drug in powder, granulate, matrix, adsorbate, or liquid form is provided as the core 11 of the taste masked formulation 10. The core 11 is surrounded by a spacing layer 12. The spacing layer itself is surrounded by a taste masking layer 13 such that the spacing layer 12 physically separates, preferably completely, the core 11 from the taste masking layer 13. Of course, other layers located between the core 11 and the spacing layer 12, between the spacing layer 12 and the taste masking layer 13, or surrounding the taste masking layer 13 are also possible so long as they do not change the basic and novel characteristics of the invention.

"Drug(s)" in accordance with the present invention can be any pharmaceutically active material and can also include vitamins, minerals, nutritional supplements and the like. These can include, without limitation systematically distributable pharmaceutically active materials, vitamins, minerals, dietary supplements, as well as non-systematically distributable pharmaceutically active materials. Drugs or pharmaceutically active materials may include, without limitation, antacids, analgesics, anti-inflammatories, anti-pyretics antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers and combinations thereof. Also encompassed by the term drug(s),are the pharmaceutically active materials described in Mantelle, U.S. Pat. No. 5,234,957, in columns 18 through 21. The text of Mantelle is hereby incorporated by reference.

As used in this disclosure, the term "vitamin" refers to trace substances that are required in the diet. For the purposes of the present invention, the term "vitamin(s)" include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMN), flavin adenine dinucleotide (FAD), Nicotinamide adenine dinucleotide (NAD), Nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,2-S-dihydroxycholecalciferol. The term "vitamin(s)" also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, (calcium carbonate), iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

In general, the amount of drug incorporated in each dosage form may be selected according to known principles of pharmacy. Dosage form means a tablet or capsule, soft gel capsule, caplet and the like. Slugged capsules are also contemplated. An effective amount of drug is specifically contemplated. By the term effective amount, it is understood that, with respect to for example pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of drug used can vary greatly. Of course, the size of the dosage form, the requirements of other ingredients, the size, age, weight, sex, condition of the patient, their medical condition and the number of, for example, tablets which constitute a single dose can all impact the upper limit of the amount of pharmactive ingredient which can be used. However, generally, the active ingredient is provided in an amount of between greater than zero and about 60% by weight of the finished tablet and, more preferably, in a range of between greater than zero and about 40% by weight thereof. Put in other terms, the active ingredient can be included in an amount of between about 1 microgram to about 2 grams and more preferably between about 0.01 and about 1000 milligrams per dosage form. The amount of drug refers only to the actual amount of drug in dosage forms containing cores of the taste-masked formulations, i.e. the core of the coated particles, as well as any other drug present. It does not include the weight of any coating. For example, if a dosage form in accordance with the present invention includes coated particles in accordance with the present invention as well as some uncoated drug, the weight of drug includes the weight of the core and the weight of uncoated drug, but not the weight of the coating. It also does not include the weight of any excipients which may be used in producing the core. Such excipients may include binders, fillers, lubricants, disintegrants, bulking agents, colors, solvents, flavors adsorbates (such as sugar spheres) or absorbates, and the like; These excipients, if present at all, can be used in convential amounts, and typically range from about 0.5% to about 95% percent by weight, based on the weight of the formulation (excipient, drug and coating). More preferably 0.1%–50% of said excipients can be present.

The weight, thickness and composition of the spacing and taste masking layers are secondary to the layers function. Any material, in any thickness and any weight, which serves the functions described are contemplated. But generally, the spacing layer can be provided in an amount of between about 5 and about 100, and preferably 20 to about 50 percent weight gain, based on the weight of cores. The taste-masking layercan be provided in an amount of between about 5 and about 100, and preferably between 20 and about 70 percent weight gain, based on the weight of the core and the spacing layer. Preferably, the spacing layer has a thickness of between about 5 microns and about 75 microns and more preferably between about 5 microns and about 30 microns.

The core can be formed by conventional methods such as, for example, granulation, spray-layering, spheronization, microencapsulation or densification (roller compaction or slugging). The core may then be coated by conventional methods with the spacing layer. The spacing layer can be composed of any material, or combination of materials, which can completely coat the drug core and prevent it from migrating, piercing or otherwise interfering with the taste masking layer. The spacing layer can be a controlled release coating. Such coating include, without limitation, an enteric coating, an extended release coating (one providing release of drugs over 12 to 24 hours or longer) or, a coating providing a pulsed (pulsitile) or targeted delivery.

In a particularly preferred embodiment, the spacing layer surrounding the core will be made of a material which allows for rapid release. Rapid release means that the coating material will pose little or no impediment to the otherwise normal dissolution and bioavailability of the drug if given in bulk form. In general, a rapid release coating will not delay dissolution by more than one half hour. More preferably, the delay caused will be less than about ten minutes. The spacing layer can be made of any material that can sequester the core from the taste masking layer. Preferably, the material will rapidly expose the core when in a patient's stomach. These materials include without limitation, modified celluloses such as ethyl cellulose, methyl cellulose, hydroxypropyl cellulose, hydroxy propyl methyl cellulose, polyalkylene glycols, polyalkylene oxides, sugars and sugar alcohols, waxes, shellacs, acrylics, etc., and mixtures thereof. Preferably these materials can provide some measure of taste masking as well. Many of these materials, alone or in combination, can provide controlled release. But, when used for rapid release, these same coatings may need to be applied in a thin layer or in combination with swelling agents, soluble materials allowing for pore formation and the like.

The taste masking layer, which may be coated over the spacing layer by conventional methods as previously discussed, must meet several criteria. First, it should be capable of rapidly dissolving in the stomach of a patient so as to rapidly expose the spacing layer. This is particularly critical when rapid release dosage forms are intended as both coatings must act in concert so as to prevent unwanted delay in the drug delivery. At the same time, the taste masking layer must, when properly sequestered from the core, prevent or delay exposure of the core, and preferably the spacing layer also, for a period of time which is sufficient to allow the dosage form to disintegrate in a patient's mouth and be swallowed. Generally, the taste masking coating must taste mask (i.e. prevent significant exposure of the spacing layer) for at least about 20 seconds, preferably 30 seconds or more, and more preferably longer than 45 seconds. This assumes a well formed coating and that the patient has saliva of greater than pH 6.5, does not excessively chew the tablet and does not ingest the tablet with significantly acidic liquids such as orange juice.

The coating should be generally insoluble in saliva, i.e. in materials having a neutral to slightly basic pH of greater than about 6.5. Generally insoluble does not require complete insolubility, however, the material needs to be insoluble enough to provide effective taste masking. However, the coating is preferably completely and generally rapidly soluble at pHs of less than about 6.5. Of course, the rate of solubility may increase with the decrease in pH.

Any material which can meet these objectives is specifically contemplated. One commercially available material useful as the taste masking layer is Eudragit E-100 (aminoalkyl methacrylate copolymer E) available from Röhm GmbH, Darmstadt, Germany. This material is generally insoluble at basic pHs. However, at neutral to slightly acidic pHs, in the range of between about 6.5 and 7.0, Eudragit E-100 can swell sufficiently to cause problems. It has been found if gatifloxacin, for example, were coated with Eudragit E-100 alone and administered to a patient whose saliva tended to be even slightly acidic, the length of time that the dosage form could remain in the patient's mouth without exposing the patient to the objectionable tasting gatifloxacin is limited. That time period is sufficiently extended by the use of the spacing layer.

It has been found that the combination of the slightly acidic pH in some patients' saliva and the coating imperfections caused by directly coating the core with the taste masking layer result in either a high immediate risk of exposure or a greatly reduced duration of taste masking. That time period can also be extended by increasing the thickness of the taste masking layer. Alternatively, other taste masking materials can be used which are more insensitive to saliva having a slightly acidic pH yet are sufficiently sensitive to pH below 6.5 to be of value. Anything that is base insoluble, but acid soluble and meets the other criteria set forth herein would be acceptable. Preferably the taste masking layer has a thickness of between about 5 and about 75 microns and more preferably about 5 and about 30 microns.

In addition, conventional excipients such as colorants, anti-tack agents, fillers, plasticizers, pore forming agents, glossing agents, etc. can be added to the material which forms any coating layer, or such materials can be added over and/or under any such layer. Generally, the amount of such materials will be between about 0–300% of the weight of the polymer, and preferably 0–100% by weight. Not only should the taste masking layer and the spacing layer complement each other in terms of the drug release profile, this cooperation should also extend to taste masking. Preferably, the spacing layer can provide some additional taste masking in the eventuality that the taste masking layer is compromised by, for example, chewing, extended exposure to saliva in the mouth, excessively acidic saliva, or coating imperfections. For some particularly obnoxious drugs, seconds can count and the taste masking ability of the spacing layer can play an integral part in preventing the exposure of a patient to a particularly objectionable medication.

Particles formed from the coated drug in accordance with the present invention may range in size from a few microns to as much as 1,500 microns. The lower limit of the size is not important, provided integrity is not compromised. Particles should generally not be larger than 1,200 microns and preferably no larger than 850 microns.

Rapid release dosage forms in accordance with the present invention are those in which the drug is rapidly released from the coatings in the stomach. To the extent possible, the effect of the spacing and taste masking layers under such circumstances will be minimal in terms of reducing the normal bioavailability of the same drug if uncoated. It is important that that coating be intact, to the extent necessary to serve its taste-masking function, while the dosage form is in the mouth of the patient. However, once the patient has swallowed and there is no longer a need to protect the tastebuds from the drug, it may be desirable that the drug be immediately bioavailable. In such a circumstance, it is desirable for the coating to either rupture in order to release its contents, dissolve thereby exposing its contents or allow the gastric juices in the stomach to permeate through and dissolve the active ingredient such that the bioavailability of the drug remains, as nearly as possible, that of the same drug if administered in an uncoated form. Thus, if a tablet including non-protected active ingredients would need to be normally dosed every four or every six hours, than the rapid release dosage form in accordance with the present invention would also have to be administered on that same basis. A rapid release dosage form in accordance with the present invention is one which disintegrates rapidly in the mouth to form a suspension of particles which will, once they clear the mouth, release their contents so as not to significantly interfere with the normal bioavailability of the active ingredient as described.

Generally, the coated particles of drug in accordance with the present invention are provided in an amount of between greater than zero to about 75% by weight based on the weight of the finished tablet. More preferably, the particles provided in an amount of between greater than zero and about 60% by weight.

The balance of the dosage form will, be either an alternative drug, either uncoated or coated by some other technology, disintegrants and/or excipient(s). In one aspect, the present invention requires the formation of a rapidly disintegratable tablet. That means that the tablet will disintegrate in the mouth of the patient in less than 90 seconds and, more preferably, in less than 45 seconds. It is therefore very important to have, contained within the formulation, a suitable disintegration agent. These disintegration agents can include, for example, microcrystalline cellulose such as: AVICEL PH 200, PH 101, Ac-di-Sol-croscarmelose sodium, PVP-XL, starches and modified starches, polymers and gums such as: Hydroxymethylcellulose, Hydroxypropylcellulose, Arabic, Xanthan, Hydroxypropylethylcellulose, and Carbopols.

The non-effervescent disintegration agent or combination of agents is generally present in an amount of between greater than zero and about 20% by weight based on the weight of the tablet. However, preferably, it is provided in an amount of between about 2 and about 12% by weight based on the weight of the finished tablet.

In addition, it may be desirable to use an effervescent couple alone or in combination with the other recited ingredients to improve the disintegration profile, the organoleptic properties of the material and the like. When used, preferably, the effervescent couple is provided in an amount of between about 2 and about 50%, and more preferably, between about 3 and about 15% by weight, based on the weight of the finished tablet. It is particularly preferred that sufficient effervescent material be provided such that the evolved gas is less than about 30 cm3, upon exposure to an aqueous environment.

The term "effervescent disintegration agent" includes compounds which evolve gas. The preferred effervescent agents evolve gas by means of a chemical reaction which takes place upon exposure of the effervescent disintegration agent (an effervescent couple) to water and/or to saliva in the mouth. This reaction is most often the result of the reaction of a soluble acid source and an alkali monohydrogencarbonate or carbonate source. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

In the case of the orally disintegrable tablets in accordance with the present invention, it is preferred that the amount of disintegration agent, either effervescent or noneffervescent or the combination thereof provided be sufficient such that the tablet provides a pleasant organoleptic sensation in the mouth of the patient. In some instances, the patient should be able to perceive a distinct sensation of fizzing or bubbling as the tablet disintegrates in the mouth. In general, the amount of either effervescence disintegration agent, noneffervescent disintegration agent or both in accordance with the present invention should be sufficient to allow for the rapid and complete disintegration of the tablet when orally administered. Disintegration time in the mouth can be measured by observing the disintegration time of the tablet in water at about 37° C. The tablet is immersed in the water without forcible agitation or with minimal agitation. The disintegration time is the time from immersion for substantially complete dispersion of the tablet as determined by visual observation. Complete disintegration of the tablet does not require dissolution or disintegration of the microparticles or other discrete materials included.

In addition to the particles in accordance with the present invention, and any disintegrant the dosage forms in accordance with the present invention may include pharmaceutically acceptable excipients flavors, diluents, colors, binders, fillers, compaction vehicles, and lubricants. The total of solid excipients will generally range from greater than zero to near 100% by weight based on the weight of the finished dosage form. Preferably, the excipients and/or the combination of excipients and disintegrants are present in an mount of greater than zero to about 95% and more preferably, bout 75% by weight of the finished dosage form.

The filler in accordance with the present invention will preferably assist in preventing the rupture of the particles during compression. The filler will also assist in the rapid disintegration of the dosage form in the mouth. Such fillers include sugars and sugar alcohols. Non-limiting examples include dextrose, mannitol, sorbitol, lactose, sucrose. The filler is, however, generally a non-direct compression filler. Dextrose, for example, can exist as either a direct compression sugar, i.e. a sugar which has been modified to increase its compressibility, or a non-direct compression sugar.

Tablet binders may be used in an amount of about 60 weight percent and preferably about 10 percent to 40 percent based on the weight of the total composition. Noneffervescent disintegrants such as, for example, starches, PVP-XL, microcrystalline cellulose and the like may also be used and may comprise up to about 20 weight percent, preferably between about two percent and about 6 percent of the total weight composition. Coloring agents used may range from between about 0.1 to 3.5 weight percent of the total composition. Flavors incorporated into the composition may be chosen from synthetic flavor oils and flavoring aromatics and/or natural oils, extracts from plants, leaves, flowers, fruits and so forth, and combinations thereof. These may include cinnamon oils, oil of wintergreen, peppermint oils, clover oil, bay oil, anise oil, eucalyptus, vanilla, citrus oil such as lemon oil, orange oil, grape and grapefruit oil, fruit essences including apple, peach, pear, strawberry, raspberry, cherry, plum, pineapple, apricot and so forth. Flavors may be present in the amount of ranging from about 0.1 to 3.0 percent. Lubricants according to the present invention may be used in the amount of up to 10 weight percent, and preferably between 0.1 and about 6 weight percent based on the total composition.

Tablet hardness is generally not important, except in the context of rapid disintegration in a patient's mouth. Therefore, traditional tableting, slugging, etc. can be used along with sufficient compression forces to produce tablets with hardness values of generally between about 10 and about 100 Newtons. Tablets, slugs for capsules and cores for solid caplets are preferred dosage forms.

EXAMPLES

Example 1

To remove the bitter taste of dextromethorphan, screen 1.2 kg of the fine powder through a 60 mesh sieve to break up any lumps. Weigh 1.0 kg screened powder into the processor bowl of a fluid bed coating apparatus fitted with a Wurster insert Spray-coat the powder to a 20% weight gain with a 70:30 mixture of ethylcellulose:PVP film solids. Taste-masking is accomplished by application of a 67:33 mixture of Eudragit E100 and powdered talc to a weight gain of 30%. Resulting beads are 5–600 µm in diameter, tasteless for approximately 30 seconds and approximately 60% potent.

Example 2

Gatifloxacin was granulated with an ethanolic solution of PVP for a final binder content of 2%. After drying, the granulate was screened to eliminate particles larger than 40 mesh and smaller than 80 mesh. 1.0 kg screened granules was weighed into the processor bowl of a fluid bed coating apparatus fitted with a Wurster insert. The granulate powder was spray-coated to a 50% weight gain with an 80:20 mixture of ethylcellulose:HPMC film solids to provide a spacing layer. A taste-masking layer was applied by application of a 67:33 mixture of Eudragit E100 and magnesium stearate to a weight gain of 70%. Resulting beads are 400–900 µm in diameter, tasteless for approximately 60 seconds and approximately 40% potent. Dissolution was about 97% in 7½ minutes and 100% in 15 minutes by USP Paddle Method 2. Dissolution of the uncoated material is 100% at 7 minutes.

Example 3

Gatifloxacin granules, prepared as describe in Example 2, are coated with three successive coatings of 80:20 ethylcellulose:HPMC to 25% weight gains (95% total weight gain). Resulting beads are tasteless for more than 30 seconds. However, drug release from the coated material is 1% at 7 minutes and 26% at 90 minutes.

Example 4

Gatifloxacin granules, prepared as described in Example 2, are coated with Eudragit E-100 to a 50% weight gain. Resulting beads are tasteless for about 5 seconds and have an extremely objectionable taste within 16 seconds.

What is claimed is:

1. A taste masked formulation which rapidly releases a drug in the stomach of a patient comprising:
    a drug-containing core;
    a taste masking layer having a thickness of between about 5 and about 75 microns composed of a material which is generally insoluble in saliva at a neutral to basic pH and completely soluble in saliva at a pH of less than about 6.5; and
    a spacing layer having a thickness of between about 5 and about 75 microns surrounding said core and substantially completely sequestering said core from said taste masking layer and being capable of rapidly exposing said core when exposed in the stomach of a patient; said taste masking layer preventing exposure of said spacing layer in the mouth of a patient for a period of at least about 20 seconds after being placed into the mouth and being capable of rapidly exposing said spacing layer when in the stomach of a patient; wherein the taste-masked formulation disintegrates in the mouth of a patient in less than 90 seconds to form a suspension of particles; wherein the coated drug-containing core generally has a diameter of no larger than 1,500 microns.

2. The formulation of claim 1 wherein said drug is a pharmaceutically active material, a vitamin, a mineral, a nutritional supplement and mixtures thereof.

3. The formulation of claim 1 wherein said spacing layer increases the weight of the core by between about 5 and about 100 percent by weight.

4. The formulation of claim 3 wherein said spacing layer increases the weight of the core by between about 20 and about 50 percent by weight.

5. The formulation of claim 1 wherein said spacing layer has a thickness of between about 5 and about 30 microns.

6. The formulation of claim 1 wherein said taste masking layer increases the weight of the core by between about 5 and about 100 percent by weight.

7. The formulation of claim 6 wherein said taste masking layer increases the weight of the core by between about 20 and about 70 percent by weight.

8. The formulation of claim 1 wherein said taste masking layer has a thickness of between about 5 and about 30 microns.

9. A dosage form intended for direct oral administration, comprising:

an effective amount of at least one drug, said drug present in the cores of coated particles, said particles including a taste masking layer having a thickness of between about 5 and about 75 microns composed of a material which is generally insoluble in saliva at a neutral to basic pH and completely soluble in saliva at a pH of less than about 6.5; and a spacing layer having a thickness of between about 5 and about 75 microns surrounding said core and substantially completely sequestering said core from said taste masking layer and being capable of rapidly exposing said core when exposed in the stomach of a patient; said taste masking layer preventing exposure of said spacing layer in the mouth of a patient for a period of at least about 20 seconds after being placed into the mouth and being capable of rapidly exposing said spacing layer when in the stomach of a patient; and at least one pharmaceutically acceptable excipient provided in an amount of between greater than zero and less than 100%, based on the weight of the finished dosage form; wherein the taste-masked formulation disintegrates in the mouth of a patient in less than 90 seconds to form a suspension of particles; wherein the coated drug-containing core generally has a diameter of no larger than 1,500 micron.

10. The dosage form of claim 9 wherein said coated particles are present in an amount of between greater than zero and about 95% by weight based on the weight of the fished dosage forms.

11. The dosage form of claim 10 wherein said coated particles are present in an amount of between greater than zero and about 75% by weight based on the weight of the finished dosage forms.

12. The dosage form of claim 9 further comprising a disintegrant wherein the amount of said disintegrant and said excipient are between greater than zero and about 95% by weight based on the weight of the finished dosage forms.

13. The dosage form of claim 12 wherein said disintegrant and said excipient are present in an amount of between greater than zero and about 75% by weight based on the weight of the finished dosage forms.

14. The taste masked formulation of claim 1, wherein the coated drug-containing core has a diameter of no larger than 1200 microns.

15. The taste masked formulation of claim 14, wherein the coated drug-containing core has a diameter of no larger than 850 microns.

16. The dosage form of claim 9, wherein the coated drug-containing core has a diameter of no larger than 1200 microns.

17. The dosage form of claim 16, wherein the coated drug-containing core has a diameter of no larger than 850 microns.

* * * * *

UNITED STATES PATENT AND TRADEMARK OFFICE
CERTIFICATE OF CORRECTION

PATENT NO. : 6,740,341 B1 Page 1 of 1
APPLICATION NO. : 09/449851
DATED : May 25, 2004
INVENTOR(S) : Kris E. Holt et al.

It is certified that error appears in the above-identified patent and that said Letters Patent is hereby corrected as shown below:

Col. 1, ln. 43, "of ten very" should read -- often very--.

Col. 1, ln. 65, "toe" should read --to--.

Col. 2, ln. 10, "taste asking" should read --taste masking--.

Col. 5, ln. 26, "0.1%-50%" should read --1%-50%--.

Col. 5, ln. 35, "layercan" should read --layer can--.

Col. 6, lns. 41-42, "from R öhm GmbH," should read --from R-öhm GmbH--.

Col. 7, ln. 59, "will, be" should read --will be--.

Col. 9, ln. 8, "mount" should read --amount--.

Col. 9, ln. 9, "bout" should read --about--.

Col. 9, ln. 54, "1.2 kg" should read --1.1 kg--.

Col. 9, ln. 57, "insert Spray" should read --insert. Spray--.

Col. 11, ln. 30, claim 9, "1,500 micron." should read --1,500 microns.--

Col. 12, ln. 4, claim 12, "fished" should read --finished--.

Signed and Sealed this

Twenty-second Day of May, 2007

JON W. DUDAS
*Director of the United States Patent and Trademark Office*